United States Patent
Lipson et al.

[11] Patent Number: 6,026,812
[45] Date of Patent: Feb. 22, 2000

[54] LIGHTWEIGHT, PORTABLE POSITIONAL LIMB SUPPORT

[75] Inventors: Walda B. Lipson, White Plains; Carl Yurdin, Port Washington, both of N.Y.

[73] Assignee: Equip for Independence, Inc., White Plains, N.Y.

[21] Appl. No.: 08/339,142

[22] Filed: Nov. 14, 1994

Related U.S. Application Data

[63] Continuation-in-part of application No. 07/902,964, Jun. 23, 1992, abandoned, application No. 08/200,858, Feb. 22, 1994, abandoned, and application No. 08/098,687, Jul. 28, 1993, abandoned.

[51] Int. Cl.$^7$ ........................................................ A61F 5/37
[52] U.S. Cl. .......................... 128/882; 5/650; 5/647; 602/20; 602/23
[58] Field of Search ........................... 602/5, 20, 21, 602/22, 23; 128/845, 846, 869, 877, 878, 879, 881, 882; 248/118, 118.1, 118.3; 5/650, 647

[56] References Cited

U.S. PATENT DOCUMENTS

| | | | |
|---|---|---|---|
| 1,632,160 | 6/1927 | Barnes | 248/118 |
| 1,799,781 | 4/1931 | Chalfant | 248/118 |
| 1,904,363 | 4/1933 | Ettinger | 602/16 |
| 1,921,987 | 8/1933 | Ettinger | 602/16 |
| 1,961,118 | 5/1934 | Ettinger | 602/16 |
| 1,973,240 | 9/1934 | Werness et al. | 27/13 |
| 2,172,178 | 9/1939 | Rosenberg | 248/118 |
| 2,282,653 | 5/1942 | Herzmark | 602/33 |
| 2,795,838 | 6/1957 | McNeely | 5/646 |
| 2,978,713 | 4/1961 | Scalzitti et al. | 128/845 |
| 3,929,309 | 12/1975 | De Vore | 248/118 |
| 4,092,043 | 5/1978 | Wieland | 297/429 |
| 4,181,297 | 1/1980 | Nichols | 128/882 |
| 4,299,213 | 11/1981 | Violet | 128/882 |
| 4,417,569 | 11/1983 | Brundy | 602/20 |
| 4,538,600 | 9/1985 | Hepburn . | |
| 4,577,623 | 3/1986 | Pecheux . | |
| 4,660,550 | 4/1987 | Bodine . | |
| 4,681,309 | 7/1987 | Lechner | 5/646 |
| 4,899,735 | 2/1990 | Townsend et al. . | |
| 5,000,168 | 3/1991 | Lipson . | |
| 5,042,508 | 8/1991 | Richard | 5/648 |
| 5,111,808 | 5/1992 | Meals . | |
| 5,111,983 | 5/1992 | Simmons | 248/118 |

OTHER PUBLICATIONS

Catalog, BeOK! Fred Sammons Inc., 1993, Upper Extremity Supports, Lower Extemity Supports, pp. 257–8, 260, 262, 263.

Catalog, AliMed, inc., Operating Room Products and Diagnostic Imaging Accessories, 1993, p. L27.

Catalog, AliMed, inc., Orthopedic Rehabilitation Products, 1994–95, pp. Q40, Q46–49, Q75.

Primary Examiner—Danton D. DeMille
Attorney, Agent, or Firm—Dorsey & Whitney LLP

[57] ABSTRACT

A lightweight, portable, positional limb support device having a limb supporter coupled to a base that supports the limb supporter. The combination contains at least one cam and a notched, load-bearing camming surface for each cam, so that the limb supporter can be adjusted in its longitudinal and vertical axes relative to the base, providing a limb support device that is capable of assuming a number of positions.

22 Claims, 8 Drawing Sheets

LIGHTWEIGHT, PORTABLE POSITIONAL LIMB SUPPORT

RELATED APPLICATIONS

This is a continuation-in-part of commonly owned, applications Ser. No. 07/902,964, filed Jun. 23, 1992 now abandoned, Ser. No. 08/200,858, Feb. 22, 1994 now abandoned, and Ser. No. 08/098,687, filed Jul. 28, 1993 now abandoned.

BRIEF DESCRIPTION OF THE INVENTION

A portable limb device with an upper-half and a bottom-half each possessing an upper and lower extension. The upper half's upper extension has two oppositely-sloping surfaces, each laterally flaring outwardly and upwardly of the vertical axis from a common region of the upper extension, whereby to form a limb support trough for supporting a limb member of a patient. The device's bottom-half has an upper extension that is fixedly associated or repositionable with the upper-half lower's extension. The bottom-half's lower extension provides a horizontally-aligned stand and base surface for the device that is aligned with the upper-half's upper extension so as to provide stability when the device is rested on or against a solid surface.

BACKGROUND OF THE INVENTION

Lipson, U.S. Pat. No. 5,000,168, patented Mar. 19, 1991, describes an advanced state-of-the-art portable limb support device that offers multi-positional capabilities. The device may be made of a variety of materials, including metals and/or plastics. A number of the embodiments specifically disclosed by Lipson require a multitude of parts to make; consequently, the fabrication of such devices tends to be expensive.

Figure 6A:
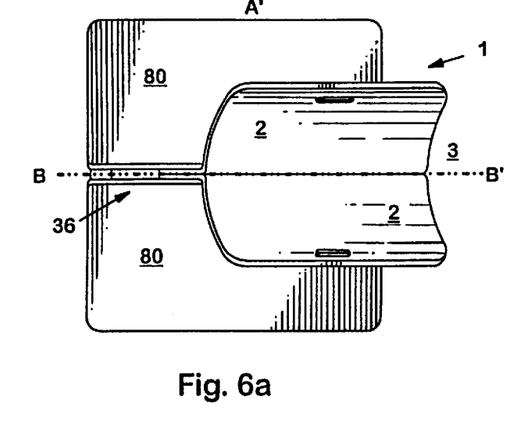
FIG. 6a is a top view of the limb support device of FIGS. 4a and b and FIG. 4b.
Figure 6B:
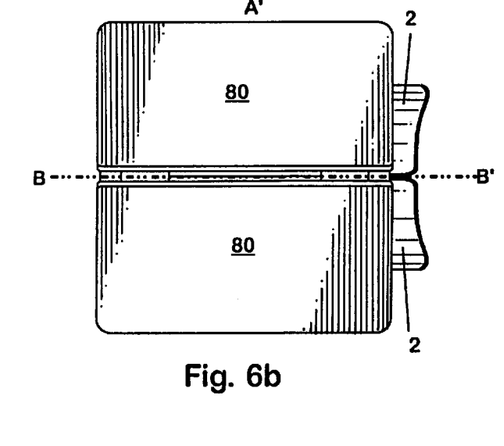

Though the Lipson patent provides a substantial degree of adjustability, there is a limitation to the levels of adjustment. For example, the conjoining arms extending from the base and the trough are telescoping tubes 44 and 46, that are limited, even in the case of FIG. 6, in the number of points of adjustment. In addition, where the tubes are frictionally engaged by a nut and bolt combination, there is a limit to the amount of weight the limb support trough can sustain, either in a single use or over a period of time.

There is a need for a multi-positional portable limb support device having some of the capabilities of the Lipson device that is simple and less costly to manufacture. There is a need for a multi-positional portable limb support device having increased adjustability and being capable of supporting the weight of a limb in the limb support trough while maintaining the desired adjustment. There is a need for a multi-positional portable limb supporter that is made by the least costly plastic fabrication processes, wholly formed of plastic, yet is durable and lightweight. In order to assure low cost, the device should be made from the minimum of parts and the parts should be easy to assemble.

THE INVENTION

The invention relates to transportable limb supporting devices for use by an ambulatory or a stationary patient, e.g., with a limb related injury. More particularly, the invention relates to a lightweight, low cost, molded transportable plastic human limb supporter (with the possible exception of fasteners and cushioning associated therewith) that contains a limb supporter capable of adjusting to a number of positions by which the limb can be supported. In a preferred embodiment, the device relies on one or more cam followers moving along notched, load-bearing camming surfaces in order to provide such adjustability and appropriate support for a limb placed in the limb supporter. The supporter has a fixed (relative to other components of the device) plastic base surface that is easily positioned either against the body (for transportability during recuperation of the patient) or on another solid surface (for stationary support of the limb). In association with the plastic base is the limb supporter formed from flared-out sections that forms a trough, with extensions from the bottom of the trough that associate with the fixed plastic base. When the limb supporter and plastic base are coupled, they form a secure plastic limb support trough.

The multi-positional portable limb supporter has many of the multi-positional capabilities of the Lipson device as well as positional capabilities not specifically described by Lipson. It is distinctive because it has a (i) lightweight and simple construction that is (ii) less costly to make, (iii) relies on one or more load-bearing camming surfaces to give significant adjustability by sliding the related cam follower over the camming surfaces, and (iv) locks the related cam follower in a position within the camming surface to attain a fixed position for the limb support trough relative to the base. The follower preferably rests under a notched camming surface to support the weight of the limb. The camming action design is simple yet provides easy adjustability and substantial support to the limb positioned in the limb support trough.

In particular, the invention relates to a portable limb device comprising an upper-half that possesses an upper and lower extension and a bottom-half (base means) that also possesses an upper and lower extension. The upperhalf is above and connected to the bottom-half and both are aligned along a plane of the vertical axis of the portable limb device. The lower extension of the upper-half extends downwardly along the vertical axis plane to connect with the upper extension of the bottom-half. The upper extension of the upper-half has oppositely-sloping surfaces configured to form an open-ended trough. Preferably, there are two oppositely-sloping surfaces, each laterally flaring outwardly and upwardly of the vertical axis plane from a common region of the upper extension, whereby to form an open-ended limb support trough for supporting a limb member of a patient. The bottom-half's upper extension is fixedly associated with the lower extension of the upper-half by embracing the lower extension of the upper-half or being embraced by the lower extension of the upper-half, thereby limiting the movement of each half relative to the other. The bottom-half's upper extension and the lower extension of the upper-half have at least one associated cam surface and cam follower such that the upper-half can be repositioned and locked within its fixed association with the bottom-half. The bottom-half's lower extension provides a horizontally-aligned stand and base surface for the device. The stand and base surface is aligned with the upper-half's upper extension so as to provide stability when the device is rested on or against a solid surface. The stand and base surface comprises flared out surfaces laterally extending out from the vertical axis plane from the bottom-half's lower extension from a common region thereof.

In a preferred embodiment, the opposing lower extension of the upper half and the upper extension of the bottom half, each aligned along the vertical axis plane are mated such that one of them provides at least one male surface and the other at least one female surface that are held in their respective positions by an adjustable fastener. Desirably, one of the lower extension of the upper half and the upper extension of the bottom half contains a camming surface and the other a cam following surface for the camming surface. Most preferably, the cam following surface is associated with a fastener that locks the opposing lower extension of the upper half and the upper extension of the bottom half into a fixed position so that the limb supporting device can effectively support a limb. In a preferred embodiment, each of the lower extension of the upper half and the upper extension of the bottom half have foreward and rearward arms oppositely positioned with respect to each other along the vertical axis plane and the respective foreward arms and the respective rearward arms are interlockable by fasteners. At least one of the foreward arms and at least one of the rearward arms contains a camming surface, preferably a notched camming surface, and the other foreward and rearward arms each contain the cam following surface such that a foreward arm can be adjusted along the camming surface within the other foreward arm and a rearward arm can be adjusted along the camming surface within the other rearward arm. Desirably, one foreward arm is inserted in the other foreward arm and one rearward arm is inserted in the other rearward arm.

Additional embodiments of the invention include the following:

1. A resilient foam bottom affixed to or associated with the bottom of the stand and base surface.
2. A supplementary stand and base surface that is detachably associated with the stand and base surface that is optionally provided with a slip resisting surface component. Typically, the supplementary stand and base surface has a larger lateral extension and greater bottom surface area than the stand and base surface, typically a surface area that is 25% greater, thereby adding further stability to the device while in use.
3. A neck and/or shoulder strap arrangement associated with the trough that helps a patient in transporting the device while bearing a limb in the trough.
4. Slip resisting surfaces provided in the trough and/or the supplementary stand and base surface.
5. The invention embraces two different variations of the limb support device of the invention. One variation is a limb support device that is specifically designed for use for supporting a patient's arm or portion thereof (hereinafter called the "upper limb supporter") and the other variation is used to support a patient's leg or portion thereof (hereinafter called the "lower limb supporter"). The primary differences between these two variations is that the upper limb supporter has a smaller stand and base surface, i.e., less surface area, and a smaller trough radius. In this embodiment, the lower limb supporter is not designed for use while the patient is ambulatory. The lower limb supporting device differs in a stand and base that has a greater surface area, lending maximum stability for supporting a patient's leg with a leg or foot injury or an injury that relates to the position of a lower limb. In addition, the trough of the lower limb supporter possess a greater diameter to accommodate the greater circumference of a leg versus an arm.
6. A blanket support that is affixed through the trough of a lower limb supporter. The blanket support is characterized as a shaped wire, rod or tubing that is affixed to both of the trough's outer sides at the upper lip of the trough's sloping side walls, that extends out from an open end of the trough and rises to a position superior in height to the foot of the limb resting in the trough, at about the location of the resting foot so that should a blanket be place over the patient's lower limb or only the foot, it will be prevented from laying on the resting foot.

The invention satisfies the need for a multi-positional portable limb supporter that is made by the least costly plastic fabrication processes, wholly formed of plastic (with the possible exception of cushioning material, fasteners, rods, nuts and bolts), durable and lightweight. The term "completely molded," as used herein, means shaping the plastic by heating it. It may be made by bending and cutting, injection molding, vacuum forming, compression molding, combinations of these processes, and the like plastic molding processes. The plastic fabrication may include the use of fiber and/or fabric reinforcement imbedded in the part for added strength, pigments and colorants and/or chemical agents that affect the performance characteristics of the plastic. A facet of this invention is that the device is made from a minimum of parts and the parts are easy to assemble to form the device. The result is a unique, low-cost limb supporter.

In particular, the invention relates to an transportable and adjustable limb support device that comprises the combination of a limb supporter coupled to a base means that supports the limb supporter, wherein the combination contains at least one notched, load-bearing camming surface with cam followers therefor, such that the limb supporter can be adjusted in its longitudinal and transverse axes relative to the axis of the base means. In particular, both the base means and the limb supporter contain forwardly and rearwardly spaced mated pairs of arms extending from them. The forward and rearward arms of the base means and the forward and rearward arms of the supporter, respectively, couple to each other. At least one of each set of forward or rearward arms are provided with a notched, load-bearing camming surface and an associated cam follower, such as a rod or roller. Any set of forward or rearward arms not provided with a camming surface and follower, is provided with a pivoting means that allows the other set of arms to move in accordance with the camming surface-cam follower relationship.

Illustrative of a specific embodiment of the invention, the supporter of the invention may contain four, molded-plastic parts comprising (A) a set of parts forming the limb support means and (B) a set of parts forming both a holder and base for (A). The limb support means (A) comprises an elongated trough formed from the combination of two molded plastic parts that are mirror images of each other and contains an upper and lower portion. The limb support means (A) is multi-positional in that it can be inclined, leveled or declined at one end relative to its other end, and repositioned at the other end by means of a cam moving along a notched, load-bearing camming surface. This combination of adjustability allows the limb support to be used at any angle of positioning, thereby maximizing user comfort. The lower portion of the limb support is engaged in the set of parts forming (B). The upper portion of the two molded plastic parts forms the trough. Each molded plastic part of (A) contains a curved section that flares out from the lower portion in an upwardly and outwardly direction and contributes to the formation of the trough. The base of (B) comprises a level platform to which is affixed a resilient cushioning material. The resilient cushioning material constitutes the bottom of the device.

BRIEF DESCRIPTION OF THE DRAWINGS

FIG. 6b is a bottom view of the limb support device of FIGS. 4a, b and 6a.

FIGS. 14 through 20 illustrate an improved upper limb supporter.

FIG. 14b is a left side view of the supporter of FIG. 14a.

FIG. 16 is a back view of the position of the supporter of FIG. 17.

FIG. 17 is a left side view of the supporter of FIG. 14 in the position shown in FIG. 16.

FIG. 18 is a bottom (base) surface view of the supporter of FIG. 14.

FIG. 19 is a top view of a support pan.

FIG. 20 are (a) top, (b) side and (c) back views of the bottom cushion material used in the supporter of FIG. 14.

FIG. 21 are (a) front, (b) side and (c) back views of the support pan of FIG. 19.

DETAILED DESCRIPTION OF THE INVENTION

The limb supporter of the present invention is a relatively small device in which the limb support trough is about five to about ten inches long. The overall height and width is of a size that allows the device to be carried in a manner shown in FIG. 11 of the Lipson patent. That figure is incorporated herein by reference. The size of the device is important to its ultimate utility which is to support a limb during recuperation. The device is multi-positional by means of at least one cam follower movable along a notched, load-bearing camming surface allowing the limb support means (A) to be inclined, leveled or declined at one end relative to its other end, and repositioned at the other end.

The weight of the device is low, in the neighborhood of about twelve ounces to about twenty-eight ounces, preferably from about fourteen to about twenty-four ounces. Weight is an important factor because the device is generally carried by the patient. This low weight and comfortable size means that the user may manipulate the device in many directions to create angles that allow the user to conveniently walk through a door, climb stairs, sit and rise, and the like activities.

Because this is a recuperative item that generally is needed to be used only once, it should be available at a low cost to the user. That is possible only if the item can be made in large volume at a low cost. In making a plastic item, assembly cost of the item can be a major cost factor. Therefore, a desirable plastic item is one that contains as few parts as possible and is easy to assemble to the full usable device. This is especially the case when the device is sold unassembled and is assembled by the user.

The invention is best described by reference to the drawings. In discussing the drawings, where an element is shown in more than one figure, it is referred to by the same numbers. As shown in FIGS. 1a, 1b, 1c, 2, 3, 4a, 4b, 6a, 6b, 14a, 14b, 15a, 15b, 15c, 16, 17, 22, 23, 24 and 25, the portable limb device of the invention comprises an upper-half 1 that possesses an upper and lower extension (2 and 4,5 respectively) and a bottom-half (base means) 36 that also possesses an upper and lower extension (6, 7 and 8). The upper-half is above and connected to the bottom-half and both are aligned along a plane B–B' of the vertical axis A–A' of the portable limb device. The lower extension of the upper-half 1 extends downwardly along the vertical axis plane B–B' to connect with the upper extension of the bottom-half 36. The upper extension of the upper-half 1 has oppositely-sloping surfaces 2 configured to form an open-ended trough 3. Preferably, there are two oppositely-sloping surfaces 2, each laterally flaring outwardly and upwardly of and from the vertical axis plane B–B' from a common region of the upper extension, whereby to form an open-ended limb support trough 3 for supporting a limb member of a patient. The bottom-half's (36) upper extension is fixedly associated with the lower extension (6 and 7) of the upper-half by embracing the lower extension (4 and 5) of the upper-half or being embraced by the lower extension of the upper-half, thereby limiting the movement of each half relative to the other. The bottom-half's (36) upper extension (6 and 7) and the lower extension (4 and 5) of the upper-half 1 have at least one associated cam surface (9 and/or 12) and cam follower (shafts of 19, 31 and/or 38, 20) (such that the upper-half can be repositioned and locked within its fixed association with the bottom-half. The bottom-half's lower extension provides a horizontally-aligned stand and base surface 8 for the device. The stand and base surface 8 is aligned axis A–A' within plane B–B' with the upper-half's upper extension so as to provide stability when the device is rested on or against a solid surface. The stand and base surface 8 comprises flared out bottom surfaces (8, 80) laterally extending from the bottom-half's lower extension from a common region (A–A' and B–B') thereof In a preferred embodiment, the opposing lower extension of the upper half and the upper extension of the bottom half, each aligned along the vertical axis plane A–A' and B–B' are mated such that one of them provides at least one male surface (4, 5) and the other at least one female surface (6, 7) that are held in their respective positions by an adjustable fastener 19, 31 and 38, 20. Desirably, one or more of the lower extension of the upper half and one or more of the upper extension of the bottom half contain a camming surface, e.g., 9, 12, and the other a cam following surface for the camming surface. Most preferably, the cam following surface (shaft of 19, 31 and/or shaft of 38, 20) is associated with a fastener (19 and/or 38) that locks the opposing lower extension of the upper half and the upper extension of the bottom half into a fixed position so that the limb supporting device can effectively support a limb. In a preferred embodiment, each of the lower extension of the upper half and the upper extension of the bottom half have foreward and rearward arms (4, 5 and 6, 7 respectively) oppositely positioned with respect to each other along the vertical axis plane B–B' and the respective foreward arms (4, 6) and the respective rearward arms (5, 7) are interlockable by fasteners (19, 38). At least one of the foreward arms and at least one of the rearward arms contains a camming surface (9 and/or 12), preferably a notched camming surface, and the other foreward and rearward arms (4, 6 and 5,7 respectively) each contain the cam following surface (such as the shaft of 19, 31 and/or shaft of 38, 20) that a foreward arm (4 or 6) can be adjusted along the camming surface 9 within the other foreward arm (6 or 4, as the case may be) and a rearward arm (5 or 7) can be adjusted along the camming surface 12 within the other rearward arm (7 or 5 as the case may be). Desirably, one foreward arm is inserted in the other foreward arm and one rearward arm is inserted in the other rearward arm.

Figures 7, 8, 9:
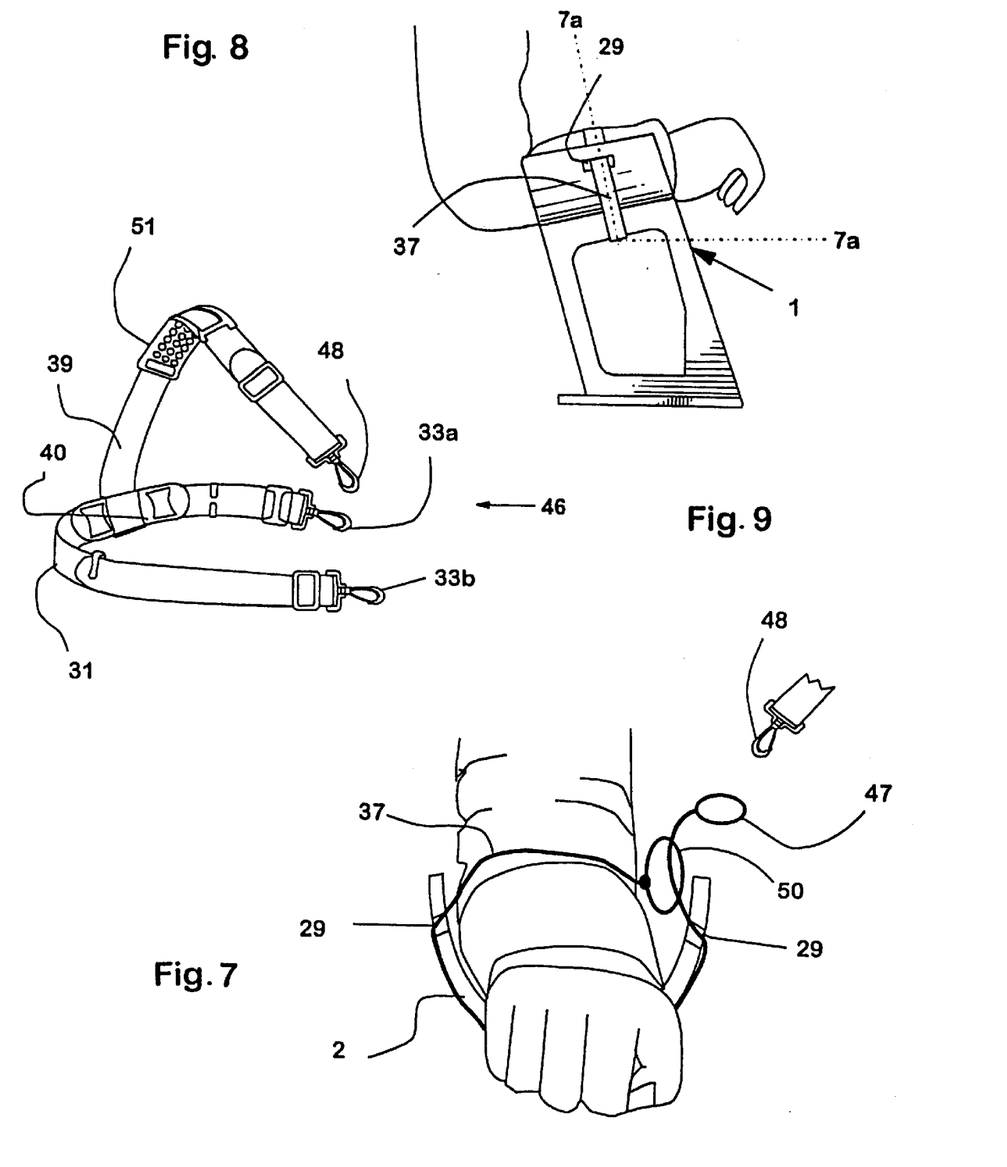
FIG. 7 is a sectional front view along lines 7a—7a of FIG. 8, except for the arm resting in the limb support device, of the limb support means with a strap holding an arm in the limb support means, and its utilization with the shoulder harness means of FIG. 9.
FIG. 8 is a side view of a multi-positional, portable limb supporter showing an arm singly strapped into the limb support means.
FIG. 9 is a shoulder harness used with a multi-positional, portable upper limb supporter.

In respect to the additional embodiments of the invention noted above, that include the following:
1. A resilient foam bottom 21 affixed to or associated with the bottom 8 of the stand and base surface.
2. A supplementary stand and base surface 22 or 58, as shown in FIGS. 10, 11, 15c, 19 and 20, that is detachably associated with the stand and base surface 8 that is optionally provided with a slip resisting surface component (not shown), such as a rectangular adhesively bonded rubber or rubber-like patch on its bottom-most surface. Typically, the supplementary stand and base surface 8 has a larger lateral extension and greater bottom surface area than the stand and base surface, typically a surface area that is 25% greater, thereby adding further stability to the device while in use.
3. A neck and/or shoulder strap arrangement, as shown in FIG. 9, associated with the trough, as shown in FIG. 7, that helps a patient in transporting the device while bearing a limb in the trough.
4. Slip resisting pad surfaces 53 provided in the trough and/or the supplementary stand and base surface.
5. The invention embraces two different variations of the limb support device of the invention. One variation, shown in FIGS. 1a, b, and c, 2, 3, 8, 12, 13, 14a, 15a, b, and c, 16, and 17, is a limb support device that is especially designed for use for supporting a patient's arm or portion thereof (hereinafter called the "upper limb supporter") and the other variation, shown in FIGS. 4a, 4b, 6a and 6b, and FIGS. 22, 23, 24 and 25 is used to support a patient's leg or portion thereof (hereinafter called the "lower limb supporter"). However, both such designs may be employed to support the other limb. The primary differences between these two variations is that the upper limb supporter has a smaller stand and base surface 8, i.e., less surface area, and a smaller trough 3 radius. In this embodiment, the lower limb supporter is not designed for use while the patient is ambulatory. The lower limb supporting device differs in a stand and base 80 that has a greater surface area, lending maximum stability for supporting a patient's leg with a leg or foot injury or an injury that relates to the position of a lower limb. In addition, the trough 3 of the lower limb supporter possess a greater diameter to accommodate the greater circumference of a leg versus an arm.
6. A blanket support 87, shown in FIGS. 24 and 25, that is affixed through the trough of a lower limb supporter. The blanket support 87 is characterized as a shaped wire, rod or tubing that is affixed (via spring clips 89, similar in construction to a paper binder clip) via an adhesive, soldered or welded bond, to both of the trough's outer sides at the upper lip of the trough's sloping side walls 2, that extends out from an open end of the trough 3 and rises to a position superior in height to the foot of the limb 85 resting in the trough, at about the location of the resting foot so that should a blanket 91 be place over the patient's lower limb or only the foot, it will be prevented from laying on the resting foot.

Figure 1A:
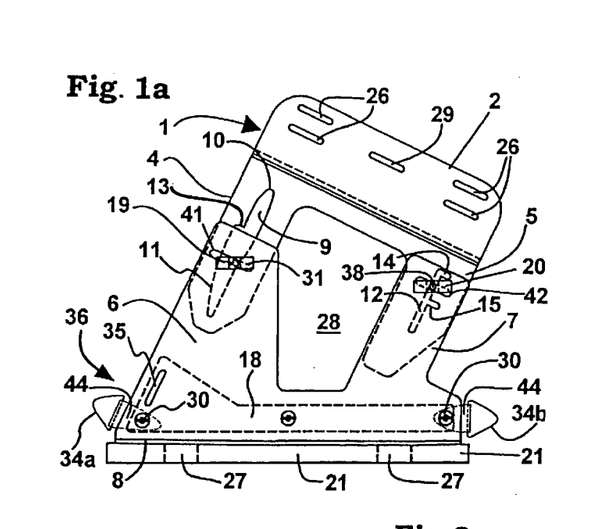
FIG. 1a is a side view of the multi-positional, portable limb supporter of the invention.
Figure 4A:
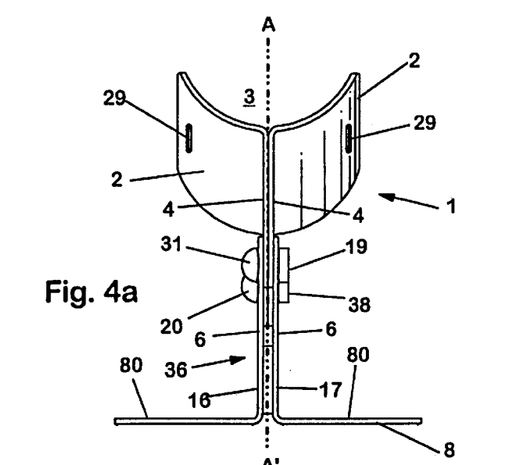
FIG. 4a is a front view of a lower limb support device of the invention
Figure 4B:
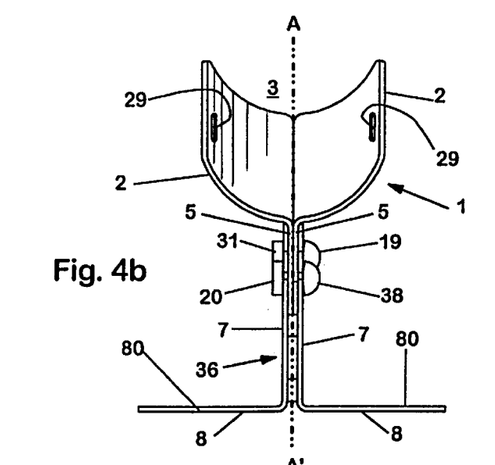
FIG. 4b is a back view of a lower limb support device of the invention.

With respect to FIG. 1a, part 1 refers to part (A) discussed above. Part 1 is shown in FIGS. 3 and 4 to be two parts held together to configure flared sections 2, located in the upper portion of part (A) as explained above, so that they form trough 3 in which a human limb can rest. Thus, the diameter of trough 3 should be at least about four to five inches across. If desired, devices can be made with different size troughs in order to provide one that most closely matches the patient's limb size. If the device is designed for leg support, as in the case with the device of FIGS. 4a, 4b, 6a and 6b, then trough 3 should be at least about five to seven inches across. Part 1 comprises the upper and lower portions of part (A). The lower portion of part (A) is shown in FIG. 5 as arms 4 and 5, held together by fastener 32, shown in FIG. 3.

Figure 1B:
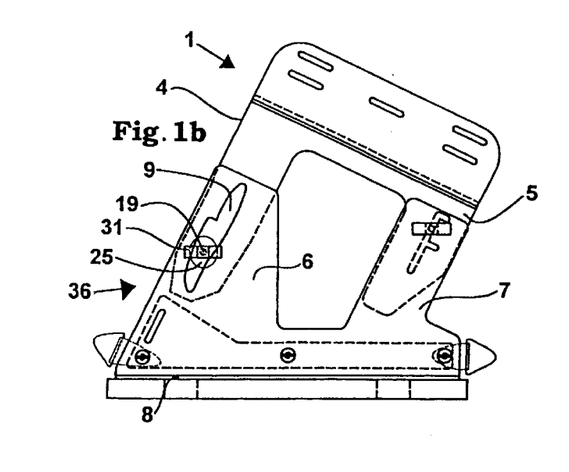
FIG. 1b is a side view of an alternative embodiment of the multi-positional, portable limb supporter of the invention.
Figures 1C, 3, 11:
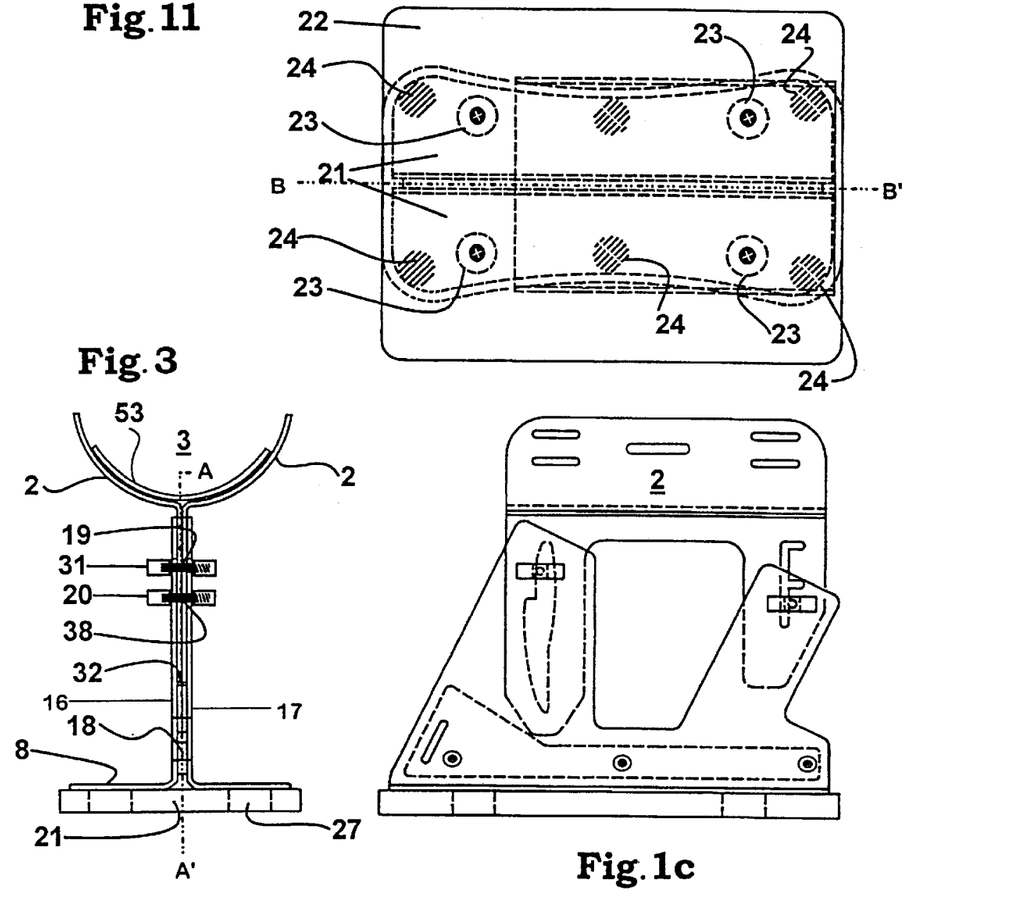
FIG. 1c shows the support device of FIG. 1a in which the limb support is repositioned.
FIG. 3 is a front view of the multi-positional, portable supporter depicted in FIG. 1c.
FIG. 11 is a top view showing the support pan resting on top of the base (bottom surface) of a limb support device.

As shown in FIGS. 1a, 1b, and 1c, arms 4 and 5 consituting the lower extension of the upper half 1, are connected to part 36, which represents part (B) discussed above. In particular, arms 4 and 5 are connected to vertically extending arms 6 and 7, respectively, consituting the upper extension of the lower half 36 which rise from the stand and base surface 8. The combination of the parts and arms forms opening 28 whose presence reduces the weight of the device. FIG. 1a and FIGS. 14a, 14b, 15a, and 15b, show side, front and back views of arms 4 and 5 inserted into slots of arms 6 and 7 with the inserted portions of arms 4 and 5 shown by dotted lines. It should be noted that arm 6 has a broad-based trapezium that narrows at its top. This allows for movement of the part (A) within part (B), as further illustrated in FIG. 1c. Also note the curved, inclined lower extremities of arms 4 and 5 which allow them to move more freely within arms 6 and 7.

Figure 2:
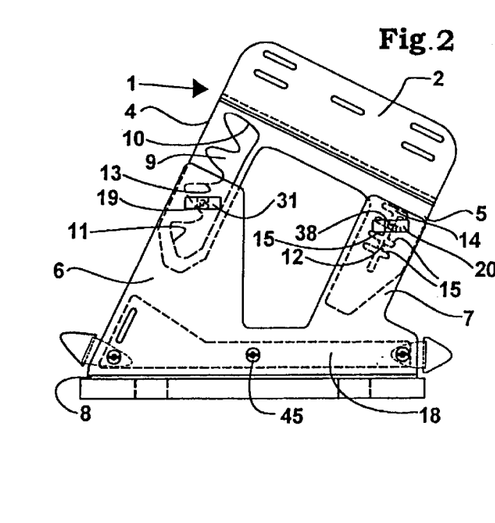
FIG. 2 is a side view of an alternative embodiment of the multi-positional, portable limb supporter of the invention with different shaped camming surfaces.
Figure 5:
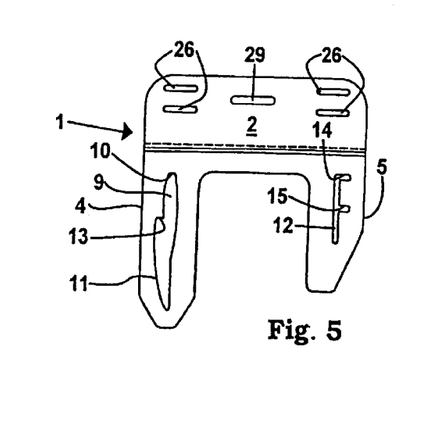
FIG. 5 is a side view of an upper half (i.e., limb support means) showing an interior notched camming surface on each arm.

As shown in FIG. 5, arms 4 and 5 each include notched, interior camming surfaces 9 and 12, respectively. The camming surface 9 of arm 4 is an offset oval shape with the lower portion 11 of the oval offset from the upper oval, forming a load-bearing notch 13 and top load-bearing surface 10. The camming surface 12 of arm 5 is in the shape of the letter "F", having two load-bearing notches 14 and 15. A variety of shapes can be used for the interior camming surfaces 9 and 12, note the modified "F" shape shown for camming surface 12 in FIGS. 14a, 14b and 17. FIG. 2 shows an alternative embodiment of the invention where camming surfaces 9 and 12 have shapes forming numerous load-bearing notches, providing a wide range of adjustability of part 1 with at least one load-bearing notch capable of providing support. In this embodiment, there are a plurality of load-bearing notched surfaces 13. Also, in this embodiment, arms 6 and 7 are over-sized, allowing arms 4 and 5 to be moved sideways to allow the cam follower shafts 19 and 38 to be nestled against a load-bearing camming surface 10, 13, 14 or 15. The irregular shapes of camming surfaces 9 and 12 allow part 1 to be adjusted to numerous positions, providing a single, adjustable device that can support limbs in a variety of positions. This configuration of the camming surfaces and cam followers therefor is suitable whether the limb supporter is an upper or lower limb supporting device.

As shown in FIGS. 3, 15a, 15b, 15c, 16, 18, part 36 comprises two, mirror-image parts 16 and 17 held together by fasteners 30 and 45 to form the bottom half 36 comprising base 8 and arms 6 and 7. As shown in FIGS. 2 and 3, a space 18 is located between parts 16 and 17 at the base of arms 6 and 7, extending along the longitudinal axis of the base 8. Above the space 18 is a gap between parts 16 and 17 that forms slotted openings. Each arm 6 and 7 includes a slotted hole opening at the top for receiving a fastener formed by matched slots in each piece 16 and 17. Optionally, those slotted holes may include matching slots 41 and 42 which allow cams 19 and 38 to be moved sideways, provided there is space in camming surfaces 9 and 12 to allow such transverse movement.

As shown in FIGS. 1a and 3, fasteners 19 and 38 provide the cam following shaft, and they extend through the holes (or slots 41 and 42, as the case may be) in arms 6 and 7 and the openings formed by interior camming surfaces 9 and 12, thereby coupling arms 6 and 7 to arms 4 and 5, providing the cam follower when in a loosened state, and locking the position of the upper half 1 when tightened. A lightweight wing nut and bolt arrangement made of plastic or metal is preferable for the fasteners. Washers 25 may be provided where the head of the bolt and the nut are smaller than the hole diameter or slot width. A plastic such as polypropylene or Delrin® (polyoxymethylene), or a metal such as aluminum, can be used for making fasteners 19 and 38.

The shaft of fasteners 19 and 38 function as a cam follower and upper half 1 is adjusted by the camming surfaces 9 and 12 moving along the shaft of fasteners 19 and 38. The shape of camming surfaces 9 and 12 with illustrated supporting surfaces 10, 13, 14 and 15, allow upper half 1 to be adjusted to numerous positions off the longitudinal horizontal axis of trough 3 or to maintain such longitudinal horizontal axis, e.g., as shown in FIG. 1c. To adjust upper half 1, the user loosens either one or both of fasteners 19 and 38 by turning wing nuts and bolts 20 and 31 to relieve pressure on arms 6 and 7. The user then adjusts trough 3 to the desired position as upper half 1 is moved by the camming action described above.

Referring to FIG. 5, the camming surfaces are load bearing when top surface 10 and notches 13, 14, or 15 rest on the cam follower shafts of 19 and 38 fitted within camming surfaces 9 and 12. In an alternative embodiment of the invention, as shown in FIG. 2, there are numerous load-bearing notches that can ride on one of the cams, each providing load-bearing support. The fasteners 19 and 38 are tightened and one of the notches rests on the cam follower, bearing the load when a limb is placed in trough 3. With this configuration, the load is transferred from upper half 1 to lower half 36 by the notch of the cam surface resting on the cam following shaft. Therefore, upper half 1 is not likely to slip out of the desired adjustment. Without loadbearing camming surfaces, the load of upper half 1 would be transferred to lower half 36 only through frictional engagement, by the tension of fasteners 19 and 38 coupling arms 4 and 5 to arms 6 and 7, respectively. After several adjustments the fasteners may become stripped, or excessive tightening of the fasteners may crack or damage the arms, resulting in a device that fails to remain in the desired position.

In FIG. 1b, showing an alternative embodiment of the invention, the coupling of the arms 4 and 5 of upper half 1 to the arms 6 and 7 of lower half 36 is partially reversed. Arm 6 contains the camming surface that in FIG. 1a is contained by arm 4. In this embodiment, camming surface 9 is molded or machined in arm 6. Fastener 19 extends through both sides of arm 4 and is locked into position by wing nuts 31 screwed onto opposite sides of the bolt component of fastener 19. The opposite ends of fastener 19 extend through camming surface 9 now cut out of the mating arm 6. Because of the size of camming surface 9, it will be desirable to provide washers 25 under the two (2) wing nuts 31 on the opposite ends of fastener 19, to assure effective tightening of the cam follower on the camming surfaces.

In a preferred embodiment of the invention and as shown in FIGS. 3, 4a, 4b, 6a, 15a, 15b, 15c and 16, bottom half 36, with the exception of resilient cushion layer 21, is two molded plastic pieces 16 and 17 that are mirror images of each other and are held together by an adhesive and/or by additional fasteners. Resilient cushion layer 21 is a relatively thick cushioning material such as polyvinyl chloride, polyurethane or latex foam that is adhesively bonded to the bottom (underside) of support surface 8. Layer 21 may be a single layer of resilient material or a laminate of resilient materials. In some cases, it may be desirable to adhesively bond a relatively nonresilient layer of a rubber or rubber-like material to the bottom of the resilient layer to assist in frictional engagement of the support to any surface. The shape of support 8 can be varied and includes those shapes shown in figures 10a, 10b, 10b and 10c of Lipson, supra.

In a further embodiment of the invention, trough 3 may contain holes of any shape in its different flared sections 2 for ventilation purposes, providing additional comfort to the user, or for providing straps to hold the limb securely in trough 3. As shown in FIG. 3, trough 3 may also include a pad 53 attached to the interior, trough-forming surface of flared sections 2 for providing a comfortable, slip-resistance surface on which the limb rests. Pad 53 may be made of latex or polyvinyl chloride foam, or any desirable material having a textured surface for comfortably cushioning a limb and that does not allow the limb to slip within the trough. As shown in FIGS. 1, 5, 12, 14a, 14b, 15a, 15b, 15c, and 17, flared sections 2 forming trough 3 may also contain a plurality of pairs of slotted holes 26—typically two pairs of them at the extremities of each flared section as shown in FIG. 5 and/or a pair of centrally-disposed slotted openings 29 in flared section 2, so that a strap or straps can be fitted between the flared sections and over the limb, holding the limb in place in trough 3.

Figure 12:
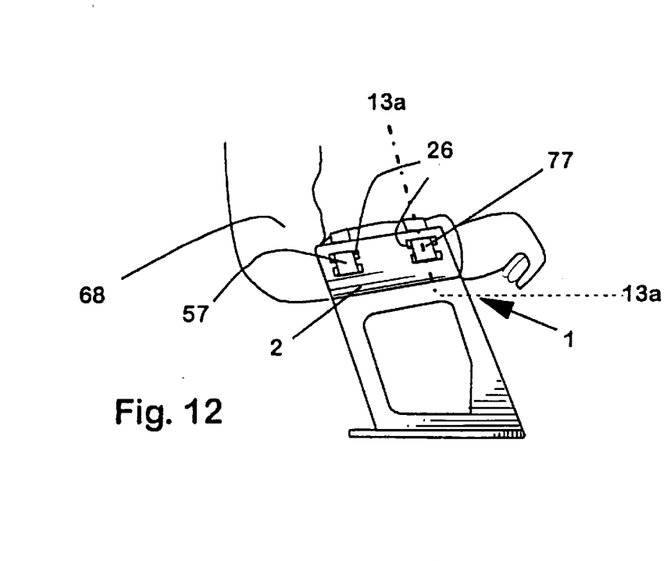
FIG. 12 is a side view of a multi-positional, portable limb supporter showing an arm doubly strapped into the limb support means.
Figure 13:
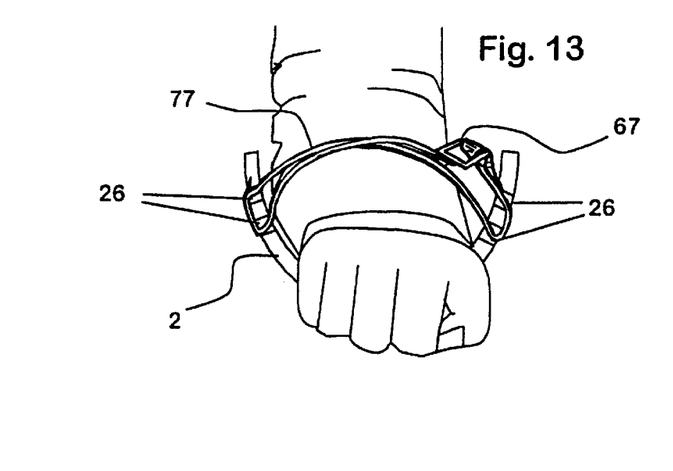
FIG. 13 is a front view of the limb supporter of FIG. 12 taken along lines 13a—13a, except for the arm resting in the limb support device.
Figure 14A:
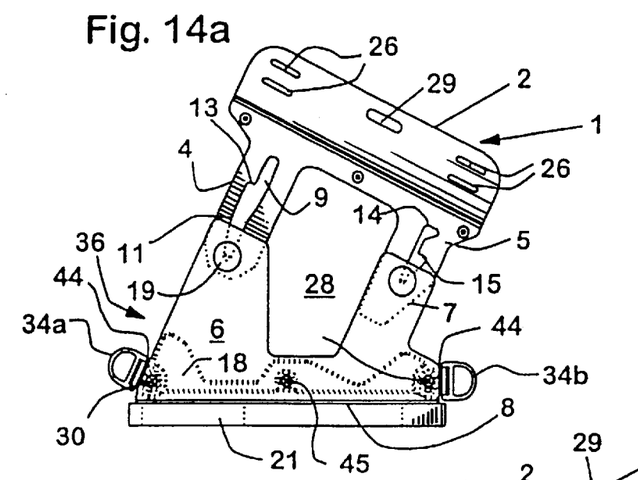
FIG. 14a is a right side view of the improved upper limb supporter.
Figure 14B:
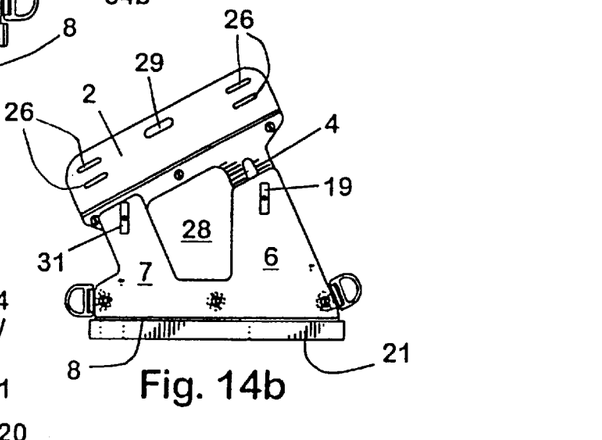

As shown in FIGS. 7, viewed along lines 7a—7a, exclusive of the limb and hand, and 8a, strap 37 that includes an "O" ring 50 at one end and a smaller "O" ring 47 at the other end is wrapped around the limb through slot openings 29, and linked by slipping ring 47 through ring 50, to secure the limb in place. Strap 37 extends through slots 29 and underneath the flared wall sections 2 and through opening 28, to surround the trough and a limb, in this example an arm. Ring 47 slips through ring 50 providing a closed loop, holding the limb in the trough 3. FIG. 8 shows a side view of the device with the users arm held in trough 3 by strap 37. Alternatively, the straps can be fitted with Velcro® adhesive fabric or metal or plastic fasteners, so that the straps can be wrapped about the limb in trough 3 and used to hold the limb in it. This is shown in FIGS. 12 and 13. In FIG. 12, an arm 68 rests in the trough formed by flared wall sections 2 of upper half 1 and is held in position by two straps. The rearward strap 57 passes through slotted openings 26 in the rearward position of the trough walls 2 and the foreward strap 77 passes through the foreward slots 26 at the foreward section of the trough walls 2. As shown in FIG. 13, viewed along lines 13a—13a of FIG. 12, exclusive of the limb and hand, strap 77 wraps through buckle 67, and due to the matching Velcro® patches on the outer and tongue section of strap 77 and an inner section as well, much like patches 90a and 90b on strap 81, strap 77 is made secure about the trough and the limb. The slotted holes can serve the dual function of also providing ventilation, adding comfort to the user. The use of "O" ring 50 has the advantage that it can be coupled to the harness of FIG. 9 by attaching clip fastener 48 to "O" ring 50.

In addition, similar slotted holes can be provided in base 8, even through cushioning 21, if desired, so that straps of the same type can be fitted to the base and used to secure the base to the user's belt, or to form a belt for the user around the user's waist, or to hold the base to another fixed object, such as a chair arm, or other support device. For example, a strap can be inserted in slot opening 35 for assisting in positioning the device, as needed.

FIG. 9 shows a harness 46 that can be used to fix the device against the users body when the device is being used to carry an arm as shown in FIGS. 7 and 8. Harness 30 includes two straps 31 and 39. Strap 31 includes fastener clips 33a and 33b, one at each end. Strap 31 extends around the users torso and clips 33a and 33b are connected to "D" rings 34a and 34b, respectively, connected via tabs 44 that are linked by fasteners 30 to the base of the device as shown in FIGS. 1a, 1b, 14a, 14b and 17. Strap 39 extends from support strip 40, over the users shoulder to the side with the immobilized arm and clip 48 is connected to "O" ring 50 of strap 37 shown in FIG. 7. Harness 30 is provided with adjustable shoulder pad 51 and adjustable harness positioner 40.

Figure 10:
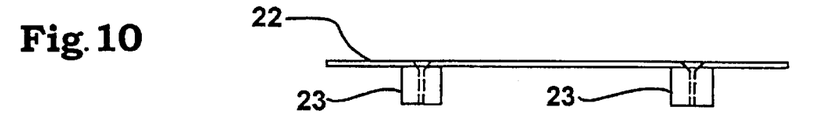
FIG. 10 is a side view of a support pan showing two of its four pegs.
Figures 16, 17, 18, 19, 20A, 20B, 20C:
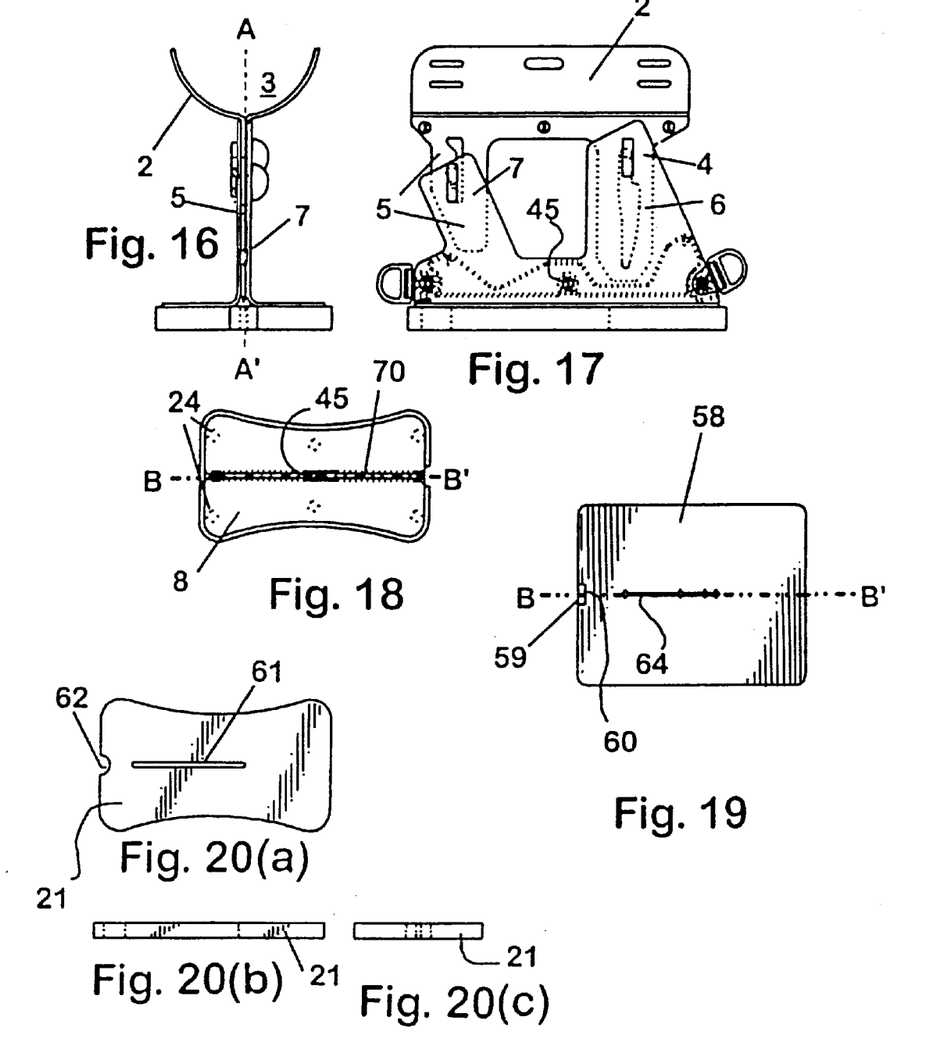

In a further embodiment of the invention, an additional pan or tray 22 may be placed on the underside of base 8 to provide additional stability and support for the device. As shown in FIGS. 10 and 11, pan 22 is a flat sheet of plastic or other suitable material with a length and width exceeding that of base 8. Pan 22 includes four upward extending pegs 23. When base 8 is placed on top of pan 22, the cushioning layer 21, above each of the four pegs 23, contains cut-out portions 27 that accommodate pegs 23, and this allows pegs 23 to conveniently fit into portions 27. The base 8 will not slide on the pan 22, but the pan 22 can be removed merely by lifting the device from pan 22. Also, FIGS. 11 and 18 show an alternative embodiment of the invention that includes six Velcro® adhesive fabric attachments 24 coupled to base 8, whereby cushioning layer 21 can be attached to and removed from the base 8. In this embodiment, the surface of layer 21 that contacts base 8 will contain a complimentary Velcro® adhesive fabric. Generally, cushioning layer 21 is adhesively bonded to the surface of base 8.

Figure 15A:
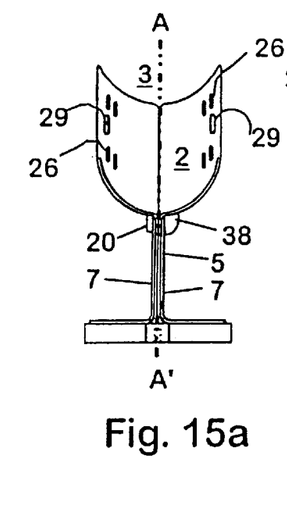
FIG. 15a is a back view of the supporter of FIG. 14.
Figure 15B:
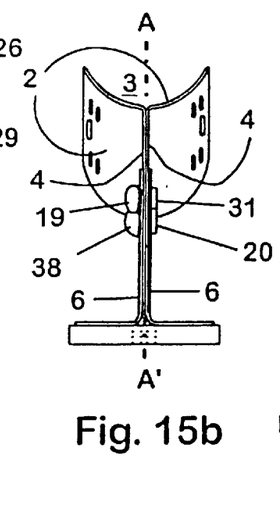
FIG. 15b is a front view of the supporter of FIG. 14.
Figure 15C:
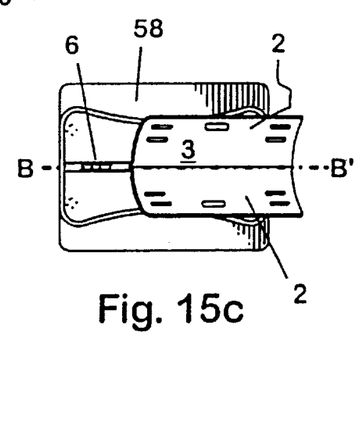
FIG. 15c is a top view of the supporter of FIG. 14.
Figures 21A, 21B, 21C:
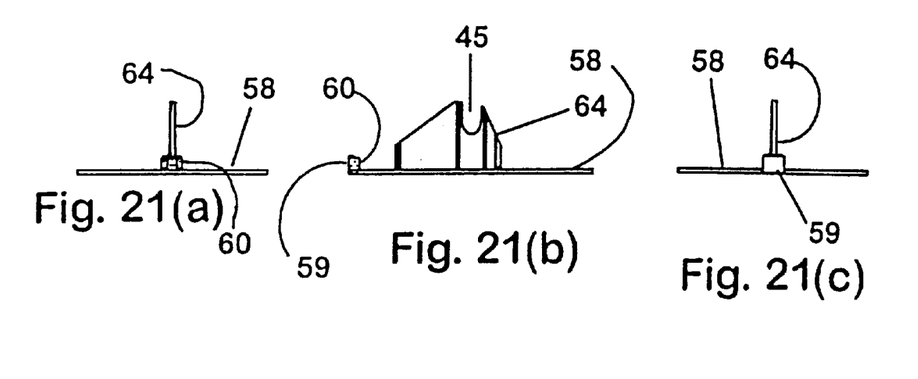
Figure 22:
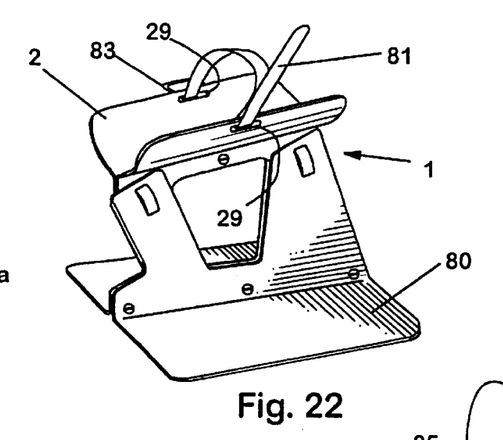
FIG. 22 is an perspective view of the lower limb supporter device of FIGS. 4a and b and 6a and b.
Figure 23:
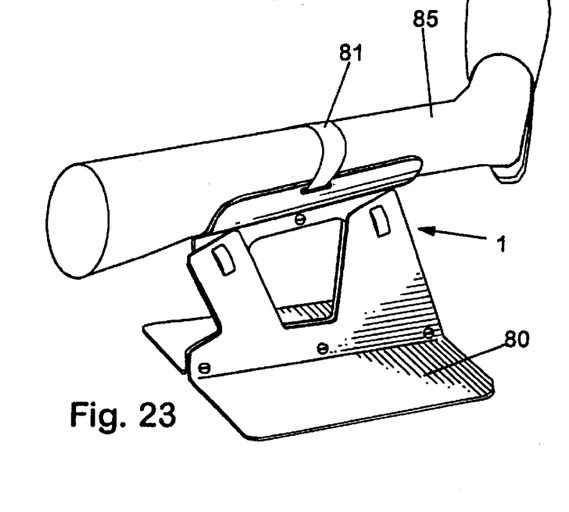
FIG. 23 illustrates a leg held in the lower limb supporter device of FIG. 22.
Figures 24, 25:
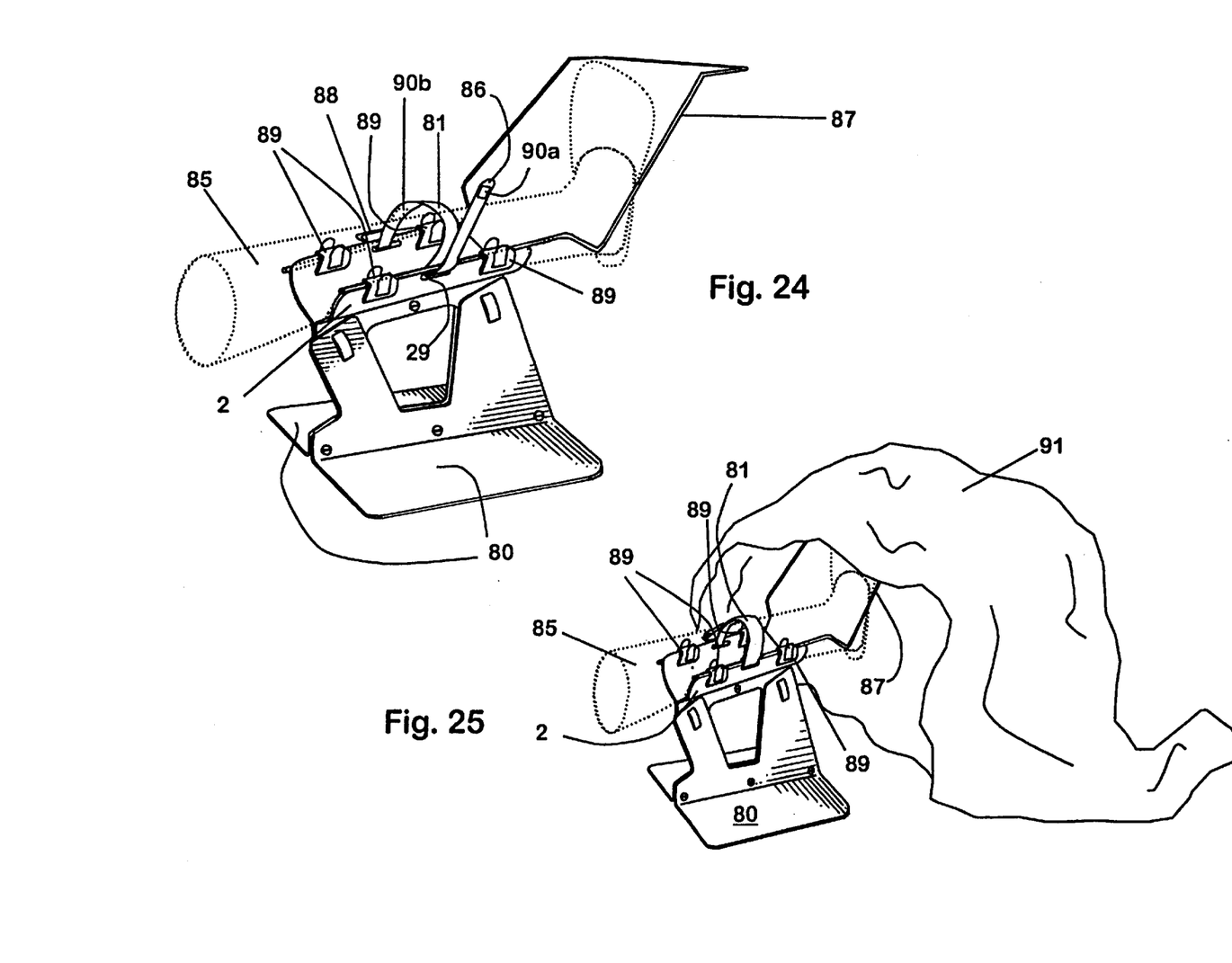
FIG. 24 is the lower limb supporter device of FIG. 22 with an attached blanket supporter.
FIG. 25 shows the lower limb supporter of FIG. 24 showing the functionality of the blanket supporter holding a blanket above the foot of the limb carried in the lower limb supporter.

As shown in FIG. 15c, a pan or tray 58 can be attached to the bottom surface 8 of limb supporter. As shown in FIGS. 19 and 21, pan or tray 58 is a flat panel that has molded as a part thereof, insert section 64, that rises in the vertical path A–A' aligned in the vertical plane B–B'. Directly to the rear, and similarly disposed is tab 60 supported by outer wall 59. Tab 60 serves as a positioner for foam sheet 21. As shown in FIG. 18 (a), (b) and (c), contains a slotted opening 61, to accommodate insert section 64, and a tab half moon opening 62, to accommodate tab 60, and thus assure alignment of pan 58 on base 8. As shown in FIG. 21 (b), insert section 64 contains four vertical rib sections to strengthen section 64. In addition, section 64 containes a semi-circular opening 65 at its top to accommodate tab 45 when the pan is inserted into the foam base 21, through base 8 into slotted opening 70 (see FIG. 18).

As noted previously, the upper limb supporter may be used to support a lower limb, if desired. In that configuration, the trough is aligned along the horizontal as shown in FIGS. 1c, 3, 16 and 17.

The limb supporters of the invention can be made by a variety of plastic molding processes. They may be made by compression molding, particularly when the supporter is made from a reinforced plastic or resin, such as a carbon fiber or glass fiber reinforced thermoset polyester or epoxy resin, a thermoplastic polycarbonate resin, a thermoplastic polyarylethersulfone resin, a thermoplastic polyarylsulfone resin, a thermoplastic polyarylate resin, and the like. Preferably, the supporter parts are made by injection molding using such thermoplastic resins as acrylic, polypropylene, polycarbonate, polyoxymethylene, polybutylene, acrylonitrile-butadiene-styrene block copolymers, and the like. Other molding processes such as transfer molding, thermoforming, pressure forming, casting, and the like, may also be used to make the limb supporters of the invention.

The present invention may be embodied in other specific forms without departing from the essential attributes thereof It is desired that the embodiments described above be considered in all respects as illustrative, not restrictive, reference being made to the appended claims to indicate the scope of the invention.

We claim:

1. A portable limb support device comprising
    a plastic-fabricated upper-half that possesses an upper and lower extension and a plastic-fabricated bottom-half that also possesses an upper and lower extension wherein
    the upper-half is above and connected directly to the bottom-half and both are aligned along a plane of the vertical axis of the portable limb device,
    the lower extension of the upper-half extends downwardly along the vertical axis plane to connect in a fixed association with the oppositely positioned upper extension of the bottom-half, thereby limiting the movement of each half relative to the other,
    the upper extension of the upper-half has oppositely-sloping surfaces extending from the plane of the vertical axis that are together configured to form an open-ended trough,
    one of (i) the bottom-half's upper extension and (ii) the upper-half's lower extension has at least one notched, load-bearing cam surface and the other of (i) the bottom-half's upper extension and (ii) the upper-half's lower extension has a cam follower fixedly associated with the cam surface which cam follower is reposition able along the cam surface and the follower moves along the cam surface such that the upper-half can be repositioned and locked in at least one of an inclined, declined, and leveled position within its fixed association with the bottom-half, the bottom-half's lower extension provides a horizontally-aligned stand and base surface for the device, the stand and base surface is aligned with the upper-half's upper extension so as to provide stability when the device is rested on or against a solid surface, the stand and base surface comprises flared out surfaces laterally extending out from the vertical axis plane from a common region of the bottom-half's lower extension.

2. The portable limb support device of claim 1 wherein the opposing lower extension of the upper half and the upper extension of the bottom half are each aligned along the vertical axis plane and are mated such that one of them provides at least one male surface and the other at least one female surface that are held in their respective positions by an adjustable fastener.

3. The portable limb support device of claim 2 wherein at least one follower is associated with a fastener that locks the opposing lower extension of the upper-half and the upper extension of the bottom-half into a fixed position so that the limb supporting device can effectively support a limb.

4. The portable limb support device of claim 1 wherein there is a resilient foam sheet affixed to the bottom of the stand and base surface.

5. The portable limb support device of claim 1 wherein there is a supplementary stand and base surface that is detachably associated with the stand and base surface.

6. The portable limb support device of claim 5 wherein the supplementary stand and base surface has a larger lateral extension and greater bottom surface area than the stand and base surface.

7. The portable limb support device of claim 6 wherein the surface area is at least about 25% greater.

8. The portable limb support device of claim 5 wherein the supplementary stand and base surface has a slip resisting surface.

9. The portable limb support device of claim 1 wherein at least one of a neck and shoulder strap arrangement is connected to the trough thereby aiding a patient in transporting the device while bearing an upper limb in the trough.

10. The portable limb support device of claim 1 wherein a slip resisting surface is provided in the though.

11. The portable limb support device of claim 1 wherein the limb support device is specifically designed for use for supporting a patient's arm or portion thereof.

12. The portable limb support device of claim 11 wherein the upper limb supporter has a smaller stand and base surface and a smaller trough radius, as compared with the corresponding dimensions of a device designed for supporting a leg or portion thereof.

13. The portable limb support device of claim 1 wherein the limb support device is specifically designed for use for supporting a patient's leg or portion thereof.

14. The portable limb support device of claim 13 wherein the lower limb, supporter has a greater stand and base surface area and a greater trough diameter, as compared with the corresponding dimensions of a device designed for supporting an arm or portion thereof.

15. The portable limb support device of claim 13 wherein a blanket support is affixed through the trough of the limb supporter.

16. The portable limb support device of claim 15 wherein the blanket support is a wire, rod or tubing that is affixed to both of the trough's outer sides at the upper region of each of the trough's sloping side walls, extending out from an open end of the trough and rising to a position superior in height to the device so that should a patient's lower limb, it will be prevented from laying on the it.

17. The portable limb support device of claim 1 wherein a blanket support is affixed through the trough of the limb supporter.

18. The portable limb support device of claim 17 wherein the blanket support is a wire, rod or tubing that is affixed to both of the trough's outer sides at the upper region of each of the trough's sloping side walls, extending out from an open end of the trough and rising to a position superior in height to the device so that should a blanket be place over a patient's limb resting in the trough, it will be prevented from laying on it.

19. The portable limb support device of claim 3 wherein each of the lower extension of the upper-half and the upper extension of the bottom-half are each comprised of a forward and a rearward arm, each of the arms being in alignment along a vertical axis plane, the forward arm from the upper extension is connected with the forward arm from the lower extension and the rearward arm from the upper extension is connected with the rearward arm from the lower extension.

20. The portable limb support device of claim 14 wherein one of the forward arms and one of the rearward arms each contain a camming surface that provides a two-dimensional position-defining contour for a corresponding follower that is included within each of the other forward and rearward arms such that one of the for be adjusted along the camming surface within the other forward arm and one of the rearward arms can be adjusted along the camming surface within the other rearward arm.

21. The portable limb support device of claim 20 wherein at least one of the camming surfaces include a plurality of load-bearing notch surfaces.

22. The portable limb support device of claim 21 wherein one forward arm is inserted in the other forward arm and one rearward arm is inserted in the other rearward arm.

* * * * *